United States Patent [19]

Wilinsky

[11] 4,438,765
[45] Mar. 27, 1984

[54] MOTION SENSITIVE FIRABLE DEVICE

[76] Inventor: Jack Wilinsky, 145 Oakdene Ave., Teaneck, N.J. 07666

[21] Appl. No.: 270,617

[22] Filed: Jun. 4, 1981

[51] Int. Cl.³ .................................. A61B 17/36
[52] U.S. Cl. .................................. 128/303.1; 128/395; 307/117; 351/209
[58] Field of Search .................. 128/303.1, 395–398, 128/419 D, 745, 782; 219/121 LB, 121 BM; 346/76 L; 351/7, 16, 158; 89/41 D, 41 L, 41 TV; 307/116, 117

[56] References Cited

U.S. PATENT DOCUMENTS

| | | | |
|---|---|---|---|
| 3,415,157 | 12/1968 | Marchisio et al. | 89/41 L |
| 3,473,868 | 10/1969 | Young et al. | 351/7 |
| 3,716,059 | 2/1973 | Welborn et al. | 128/419 D |
| 3,863,239 | 1/1975 | Campman | 307/117 |
| 3,864,030 | 2/1975 | Cornsweet | 351/7 |
| 4,122,853 | 10/1978 | Smith | 128/303.1 |
| 4,145,122 | 3/1979 | Rinard et al. | 351/7 |
| 4,346,991 | 8/1982 | Gardner et al. | 128/745 |

Primary Examiner—Edward M. Coven
Assistant Examiner—Max F. Hindenburg
Attorney, Agent, or Firm—Hane, Roberts, Spiecens & Cohen

[57] ABSTRACT

A motion sensitive firable device includes an opthomological laser for firing at an eye, switching means for activating the laser and motion detector means interconnecting the switching means and the laser for preventing the switching means from activting the laser when the motion detector means detects a given motion of the eye.

10 Claims, 1 Drawing Figure

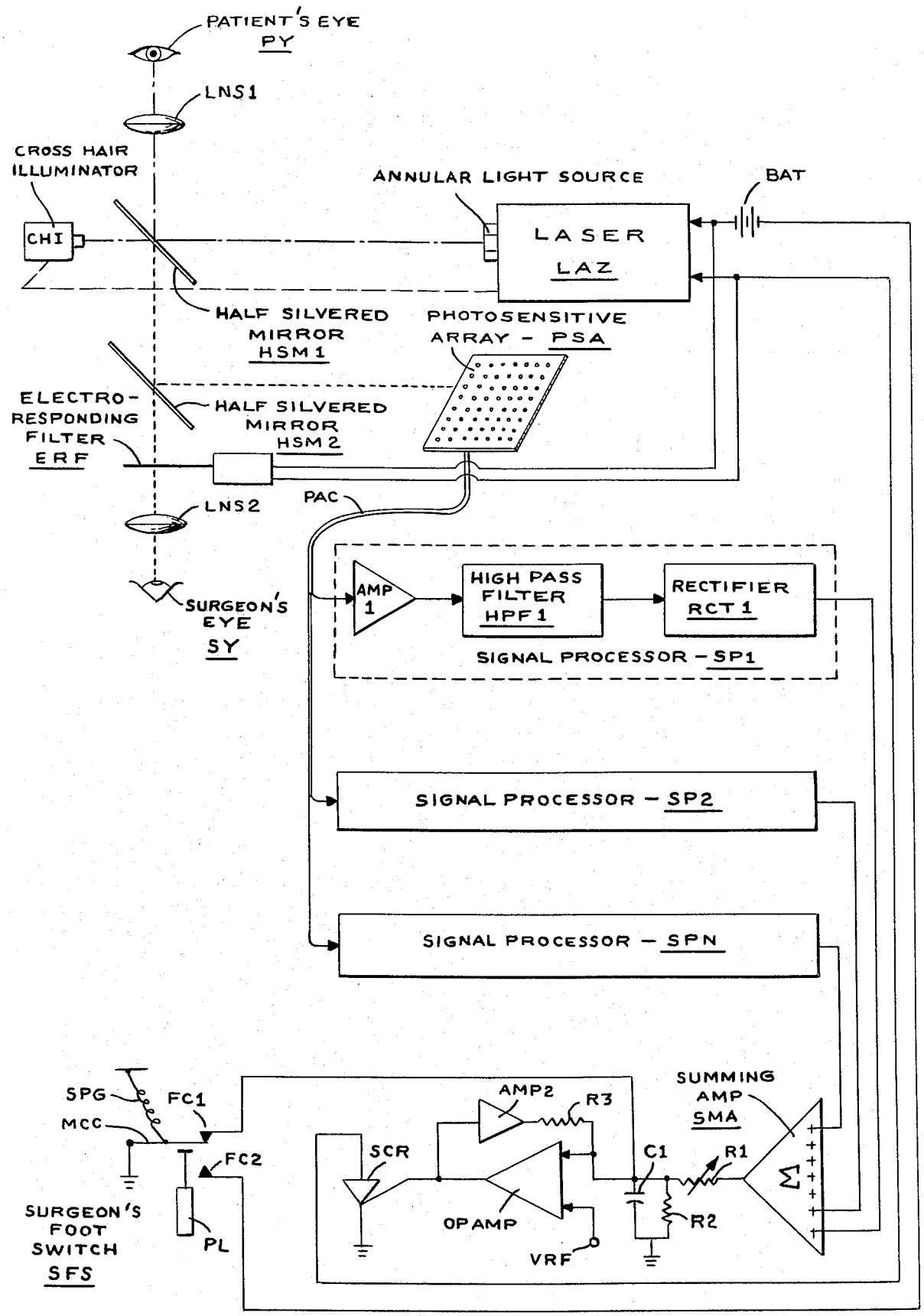
OPTHOMOLOGICAL LASER SYSTEM — OLS

MOTION SENSITIVE FIRABLE DEVICE

BACKGROUND OF THE INVENTION

This invention pertains to firable devices and more particularly to those devices whose firing is ultimately controlled by the movement of the target.

The need for controllable firable devices is present in many fields. A very significant field pertains to opthomalogical surgery and particularly to the controllable firing of lasers in such surgery. In order to perform retinal surgery using a laser it is customary for the surgeon to effectively aim the laser at the retina and when it is properly aimed to then fire the laser. However, there exist the problem that between the time that the surgeon is satisfied with the aiming and the time he actually fires the laser there has been a movement of the eye which then exposes a different site to the laser. Such a change in sites can be extremely hazardous. In order to minimize this problem surgeons quite often anaesthetize the patient. However, this can lead to further problems.

SUMMARY OF THE INVENTION

It is accordingly a general object of the invention to provide apparatus which even though activated to fire at a target can still be prevented from firing if the target moves before the firing occurs.

Briefly, the invention contemplates a motion sensitive firable device comprising firing means for firing at a target, switching means for activating the firing means, and motion detector means interconnecting the switching means and the firing means for preventing the activating of the firing means when the motion detector means detects a given motion of the target in spite of the operation of the switching means.

BRIEF DESCRIPTION OF THE DRAWING

Other objects, the features and advantages of the invention will be apparent from the following detailed description when read in conjunction with the accompanying drawing whose sole FIGURE shows the presently preferred embodiment of the invention.

DETAILED DESCRIPTION OF THE PREFERRED EMBODIMENT

The opthomalogical laser system OLS is shown schematically in the sole FIGURE in conjunction with a schematic representation of the patient's eye PY and the surgeon's eye SY.

In general, the patient's face is mounted with the eye under consideration opposite the lens system LNS1. The surgeon then positions his eye SY opposite the lens system LNS2 to provide direct viewing to the patient's eye. Then a cross-hair illuminator is moved for aiming the laser LAZ. The laser LAZ is mechanically ganged to the illuminator CHI. Surrounding the output of the laser LAZ is an annular light source. The light from this source is reflected off half silvered mirror HSM1 through the lens system LNS1 to illuminate the patient's eye for aiming. Now the surgeon starts moving the cross-hair illuminator to position the cross-hair on the target site. As he moves the illuminator he effectively moves the firing path of the laser. The illuminated cross-hairs are reflected from the other side of the half silvered mirror HSM1 through half silvered mirror HSM2 the filter ERF through the lens system LNS2. Included in the optical path of lens system LNS2 is an electroresponsive filter ERF which effectively turns opaque when electrically energized. The electrical energization will occur when the laser is fired. Since the optical system and the aiming system form no part of the invention they will not be discussed in detail.

The remainder of the opthomalogical laser system OLS includes the photosensitive array PSA which faces the half silvered mirror HSM2 to pick up light signals from the patient's eye PY. The photosensitive array PSA is preferably a matrix of photodiodes (instead of using photodiodes one could equally use the series combination of a voltage source and a photo-resistor). Each of the photodiodes is connected via the cable PAC to one of the signal processors SPN. A typical signal processor SP1 includes an amplifier AMP1 whose output feeds a high pass filter HPF1 connected to a rectifier RCT1. The high pass filter HPF1 has the function of actually controlling the thresholds of velocity to which the device will respond. As the patient's eye moves the signal emitted by any photodiode will change. The faster the movement the higher the frequency of the transient signals. Therefore, by controlling the cutoff frequency of the high pass filter one in effect controls the velocity sensitivity. In any case the DC signals fed from all of the signal processors are added by a summing amplifier SMA. The sum signal is fed via the low pass filter R1-C1 to one input of an operational amplifier OPAMP. The second input of the amplifier is a reference voltage. The output of the amplifier controls the silicon controlled rectifier SCR and is also fed back via the amplifier AMP2 to the input of the OPAMP. The combination of the comparator OPAMP and the amplifier AMP2 form a latchable comparator. It should be noted that by varying the value of the resistor R1 one then senses for the duration of the movement. Thus by increasing the value of the resistor R1 one permits a greater duration of motion. The voltage VRF fed to the other input of the operational amplifier OPAMP is used to raise the tripping voltage above the residual optical or electrical noise components. Thus by choosing the cutoff frequency of the high pass filter in the signal processors and the value of the resistor R1 distinctions can be made between gross motion and vibration since if the maximum velocity in both cases is the same the average velocity for vibration will be less than for gross motion, that is in the case of vibration, while the retina is changing velocity (direction) the capacitor C1 will be discharged through the resistor R2. Thus in this way the control of the conductivity of the silicon rectifier SCR is obtained. It is the conductivity of this rectifier which in effect eventually controls whether the laser will fire or not when the surgeon operates the footswitch SFS.

The footswitch SFS is a single-pole double-throw switch having its common contact MCC connected to ground, its normally closed contact FC1 connected to the input of the operational amplifier OPAMP and its normally open contact connected via a battery to one input of the laser LAZ. The common contact MCC when depressed will initially abut a plunger PL before making contact with contact FC2. The current return from the laser is connected to the anode of the silicon controlled rectifier SCR whose cathode is grounded.

In operation when the surgeon has aimed the laser to his satisfaction he will start depressing the footswitch FSC. At that time the input to the OPAMP will be ungrounded. As the footswitch moves, it abuts against plunger PL. At that time the surgeon decides whether the target position is still correct. If so he presses against the plunger resistance until the contacts MCC and FC2 are shorted together. The contact FC2 will be grounded and there will be established a circuit from ground to the negative terminal of the battery BAT through the laser and back to the anode of the silicon controlled rectifier SCR. If no motion is detected the SCR is conducting and the laser will fire. However, if motion is detected the OPAMP is triggered and the silicon controlled rectifier is "opened" and the laser will not fire. If on the other hand when the plunger abutment point is reached the surgeon is unsatisfied with the position of the target he releases the pressure on the switch and contact FC1 is grounded. The latch is cleared when the contact FC1 is grounded to ground the input to the operational amplifier. It is also possible to connect to the circuit a warning light or bell to indicate to the surgeon that motion was detected and the laser did not fire upon operation of the footswitch.

While only a single embodiment of the invention has been shown and described in detail there will now be obvious to those skilled in the art many modifications and variations satisfying many or all of the objects of the invention but which do not depart from the spirit thereof as defined in the appended claims. For example, while the embodiment disclosed concerns the control of opthomological lasers the same inventive concepts could be used in photography or in the firing of weapons. For example, in photography one could control the taking of still pictures to prevent the operation of the camera if any motion is detected. Similarly, for time exposures if motion is detected during the time exposure the camera can be caused to fire so that an underexposed sharp picture is obtained instead of a correctly exposed blurred picture. Furthermore, although the invention has been described with respect to optical energy it should be apparent that other types of radiation such as microwaves could also be sensed. Furthermore, in many cases it might be useful to adjust the field of sensitivity. For example, of one is sighting an object with a background in motion one might desire to restrict the field of sensitivity to exclude the background.

It should also be noted that by using conventional multiplexing techniques the cost of manufacture can be reduced.

What is claimed is:

1. A target motion sensitive firable device comprising a surgical laser for firing at a target, user operable switching means for activating said surgical laser when operated by a user, motion detector means interconnecting said switching means and said surgical laser for preventing said switching means from activating said surgical laser in response to the operation by a user when a motion is detected in the target.

2. The firable device of claim 1 wherein said motion detector means is means for detecting a motion having a velocity greater than a given velocity.

3. The firable device of claim 1 wherein said motion detector means is means for detecting a motion having a duration greater than a given duration.

4. The firable device of claim 1 wherein said motion detector means comprises a matrix of photoelectric devices each having optically sensitive areas with an operative dimension equal to the average width of a retina blood vessel image.

5. The firable device of claim 1 wherein said motion detector means further comprises a plurality of signal processing means each connected to one of the photoelectric devices for producing a DC signal related to the motion of the target.

6. The firable device of claim 5 wherein said signal processing means includes high pass filter means for selecting velocities of motion of the target greater then a said given velocity.

7. The firable devices of claim 5 wherein said motion detector means comprises signal summing means for adding all the DC signals from all of said signal processing means to a composite signal.

8. The firable device of claim 6 wherein said motion detector means comprises signal summing means for adding all the DC signals from all of said signal processing means to a composite signal.

9. The firable device of claim 7 wherein said motion detecting means comprises latchable comparator means connected to said signal summing means and operative in accordance with the amplitude of the composite signal to control the activation of said firing means.

10. The firable device of claim 1 wherein said switching means includes a mechanically operable switch having a mechanically resistive intermediate position which must be overcome before said switching means is unconditionally operative.

* * * * *